United States Patent [19]

Asher

[11] 4,419,077

[45] Dec. 6, 1983

[54] ORTHODONTIC FACE-BOW AND METHOD OF PREVENTING INJURIES WITH THE USE OF FACE-BOWS

[76] Inventor: Sidney Asher, 165 Keswick C at Century Blvd., Deerfield Beach, Fla. 33441

[21] Appl. No.: 462,665

[22] Filed: Jan. 31, 1983

[51] Int. Cl.$^3$ .............................................. A61C 7/00
[52] U.S. Cl. ........................................................ 433/5
[58] Field of Search ........................................ 433/5, 6

[56] References Cited

U.S. PATENT DOCUMENTS

| 3,087,245 | 4/1963 | Asher | 433/5 |
| 3,121,953 | 2/1964 | Asher | 433/5 |
| 3,230,621 | 1/1966 | Lindquist et al. | 433/5 |

Primary Examiner—Robert Peshock
Attorney, Agent, or Firm—Sidney Asher

[57] ABSTRACT

An improved orthodontic face-bow and method for preventing eye and facial injuries. The face-bow applies force to a patient's teeth through an orthodontic arch wire fixed to the patient's teeth. The face-bow comprises a frame having a pair of rearwardly extending arms each terminating in hooks at their rear ends and in a central frame portion at their forward ends. Rearwardly or upwardly extending spaced levers with forked ends are secured to the frame adjacent. The levers are removably connected to the arch wire. The face-bow includes an auxiliary arch wire secured to the frame adjacent the central frame portion. The auxiliary arch wire comprises auxiliary arms extending rearwardly from the central frame portion. The ends of the auxiliary arms are removably positioned in association with a buccal tube fixed to a molar. The auxiliary arch wire prevents accidental removal of the face-bow from a patient's mouth, thereby to prevent eye and facial injuries.

14 Claims, 6 Drawing Figures

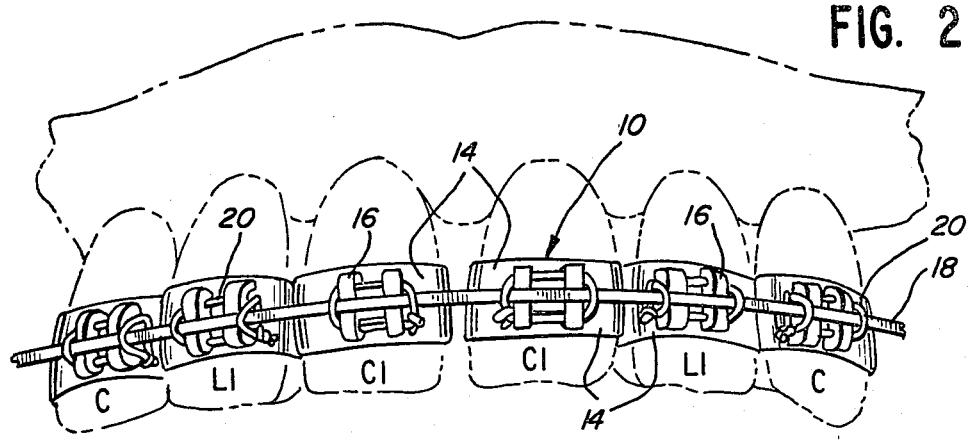
FIG. 2
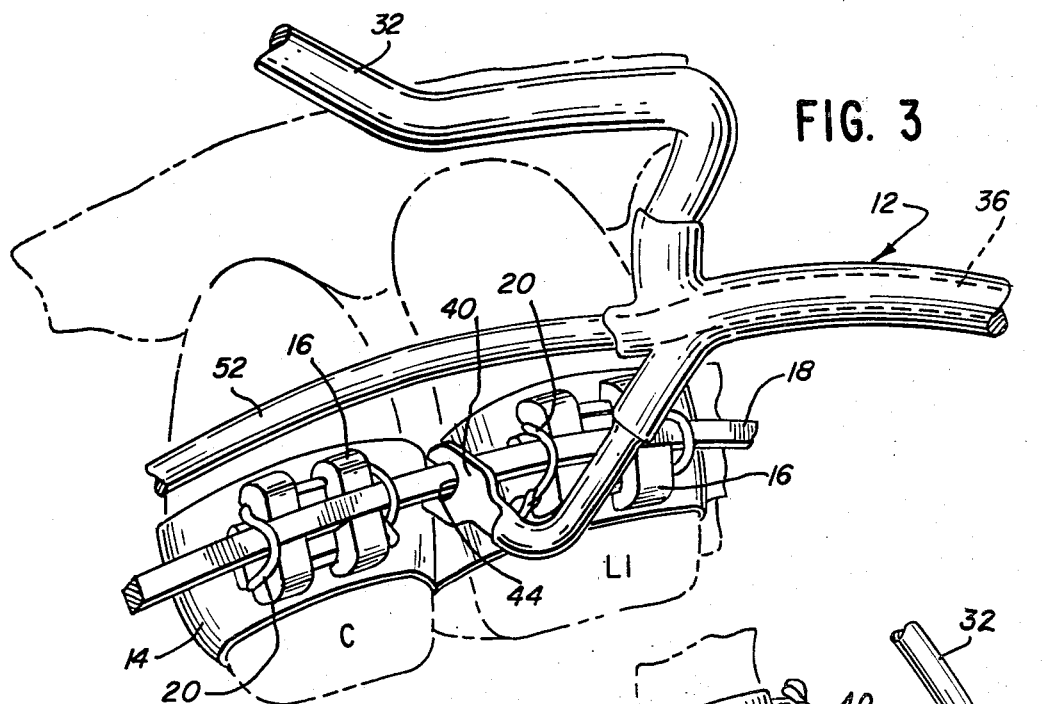
FIG. 3
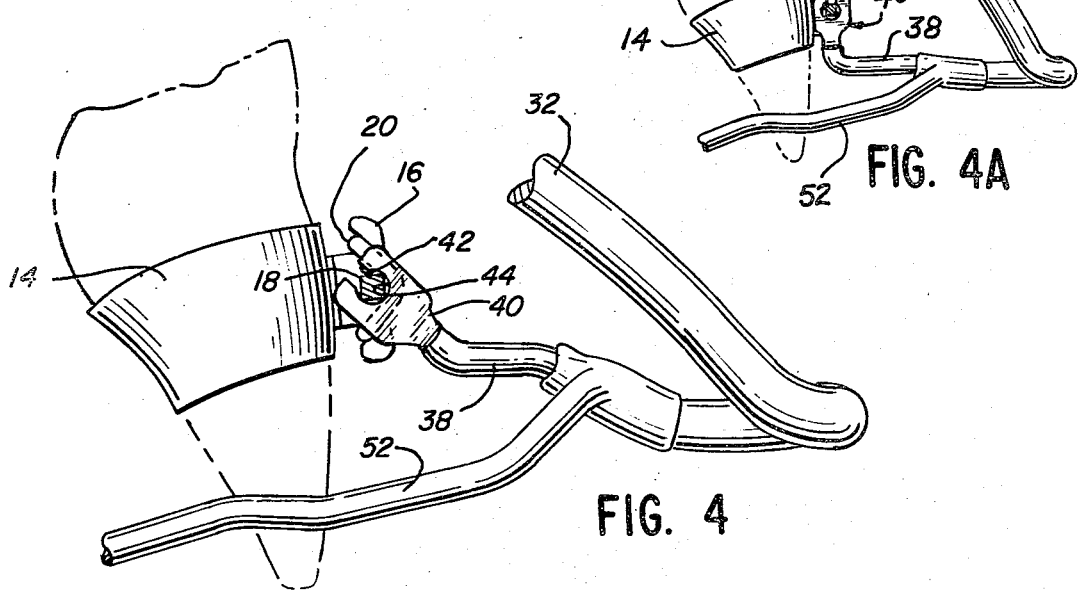
FIG. 4A
FIG. 4

ORTHODONTIC FACE-BOW AND METHOD OF PREVENTING INJURIES WITH THE USE OF FACE-BOWS

This invention relates to improved orthodontic methods and means for correcting and finishing the alignment and positioning of teeth, particularly the upper teeth, at the beginning, during, and at the end of orthodontic treatment, and particularly to orthodontic face-bows which are improved both in their corrective capabilities and in their safety of use.

BACKGROUND OF THE INVENTION

For many years orthodontic arches, colloquially known as "braces," have been applied to patients' teeth by orthodontists and by dentists to assist in correcting a variety of conditions. By making adjustments in selected parts of the arches and by using various supplemental tools and appliances, orthodontists and dentists have been able to effect changes in patients' mouths, when changes are necessary from a functional viewpoint or desirable from a cosmetic or aesthetic point of view. Orthodontic face-bows are one class of appliances which has been used to bring about desired changes in a number of types or classes of malocclusion.

An orthodontic face-bow can be described generally as a supplemental appliance which may be adjusted periodically by an orthodontist or dentist and which is readily and easily attachable to, and removable from, an orthodontic arch by the patient himself. A face-bow is constructed so that a portion is attachable to the arch and a further portion extends outside of the patient's mouth. The external portion is fastened around the patient's neck or the back or top of the patient's head where it is activated by a suitable elastic, such as by and through an elastic neck strap or head harness. In most cases an orthodontic face-bow is used at night and in the privacy of a patient's home. In severe cases, or where the patient is amenable, the face-bow can be worn around-the-clock, particularly during the first three to six months of treatment. Applicant's U.S. Pat. Nos. 3,087,245; 3,121,953; and 3,186,089 disclose face-bows and method of treating conditions requiring correction. Such face-bows have been effectively used.

In some cases, and in treating some conditions, it has been found necessary to use, in sequence, a conventional face-bow and thereafter a high-pull face-bow. For example, in cases of deep overbite where there is insufficient space in the upper dental arch, it has been necessary to use a conventional face-bow for as much as six to eighteen months to open the arch, and thereafter to use a high pull face-bow to level off a steep occlusal plane. In some such cases, rather than to take the time necessary for the sequential treatment, upper bicuspids have been removed to provide the necessary space to accommodate the anterior teeth.

Further, very recently, face-bows made by some manufacturers, because of failure to give proper instruction in their use, have been said to have caused serious injury to the eyes and faces of patients. Because face-bows are secured to the head or neck by an elastic strap or bands (and in high-pull face-bows of an elastic to the head), if the strap is not removed and one attempts to lift the face-bow over the head and loses his grip, it is apparent that upwardly or rearwardly projecting portions of the face-bow can contact the face or eyes. Such misuse of face-bows and the failure to remove the elastic before removal of the face-bow from the orthodontic arch has allegedly resulted in the loss of sight by patients in several situations.

In accordance with the present invention, not only is the face-bow more efficacious for its intended functional purposes, but it is also so constructed that it may not be removed either accidentally without first removing the elastic, nor may it purposefully be removed without first disengaging the elastic. As such, when the face-bow of this invention is used it will prevent the types of eye and facial injuries which have recently occurred.

One of the principal corrective techniques for which the face-bow of this invention may be used is that of correcting cases of deep overbite and maxillary protrusion cases, commonly known as "buck teeth." Another primary technique with which the face-bow of this invention may be used is in the flattening of the maxillary occlusal plane where a patient's occlusal plane is pitched steeply downwardly. By a steep downward pitch is meant that the plane in which a patient's teeth occlude is one which is angled sharply downwardly from the posterior to the anterior regions of the patient's mouth. By reducing the downward slope of the plane of occlusion, the final occlusion achieved by various corrective techniques tends to be more stable and more permanent as well as providing a more aesthetic occlusion. Additionally, distal driving, the rearward driving of crowns and roots of the teeth, may also be accomplished, if desired, with a face-bow embodying the principles of this invention.

With the face-bow of this invention, it is possible to secure more rapid, more effective, more uniform, more positive and more permanent correction of a deep overbite case than has been possible in the past. In part this is because stronger forces may be employed to bring about a change and modification of the maxillary bone structure, thereby achieving more rapid, desired orthopedic-orthodontic results. This has the potential of substantially reducing the time needed for wearing braces because orthodontic tooth movement may be accelerated by reorientation of the arch-tooth configuration in all sections of the maxillary arch simultaneously. As will appear, the entire maxilla may be driven rearwardly simultaneously by providing means for acting against both the anterior teeth and molars at the same time, all without necessitating the extraction of teeth, such as bicuspids, as is frequently done.

SUMMARY OF THE INVENTION

The face-bow of the present invention provides both a critically important safety feature and, if desired, means for acting on all of the teeth of the maxillary arch simultaneously. It provides for accelerated treatment, when desired, of an entire arch, and in a manner not possible with any single face-bow presently available to the orthodontic art.

Thus, the face-bow of the present invention includes lever means for acting against the arch wire of "braces" preferably to drive the anterior segment upwardly. The face-bow also includes an auxiliary arch wire for applying driving forces to the molars if needed. The auxiliary arch wire is configured to engage molar or buccal tubes and to apply force thereagainst, simultaneously with the application of force against the anterior segment via the levers, thereby to assist in the reorientation of the bone structure of the entire maxillary arch. This is especially beneficial where more space is needed for the anterior segment for effective correction. Thus force may be simultaneously applied both to the arch wire and to the molars to which the buccal tubes are secured, so that correction, as of an overbite condition, may proceed simultaneously with the opening up of additional needed space, rather than first providing space, as by driving the molars rearwardly (or extracting teeth), and then, after many months, first acting to correct, as needed, the condition of the anterior segment. To enhance the safety of use of the face-bow, the rearmost ends of the auxiliary arch wire are received within passages in the buccal tubes. This helps defeat removal of the face-bow from the mouth without first removing the activating elastic.

In accordance with this invention there is provided an improved orthodontic face-bow adapted to apply force to a patient's teeth through an orthodontic arch fixed to the patient's teeth. The face-bow is adapted to be removably connected to the orthodontic arch. The face-bow comprises a frame having a pair of upwardly or rearwardly extending arms each terminating in hook means at the rear end and in a central frame portion at their forward ends. The face-bow further includes rearwardly or upwardly extending spaced levers secured to the frame adjacent the central frame portion. The levers are removably connectable to the arch. The face-bow also includes an auxiliary arch wire secured to the frame adjacent the central frame portion. The auxiliary arch wire comprised auxiliary arms extending rearwardly from the central frame portion. Each auxiliary arm has an end portion adapted to be removably positioned in association with a buccal tube fixed to a molar, thereby securing the face-bow against removal from a patient's mouth without first removing the elastic holding the face-bow to the patient's head. Preferably the orthodontic arch includes brackets secured to a patient's teeth, buccal tubes secured to a patient's molars, and an arch wire secured to the brackets and buccal tubes. End portions of said auxiliary arms are removably disposed in passages in the buccal tubes.

In the preferred form the auxiliary arms comprise means adjacent the auxiliary arm end portions for bearing against and applying force against the buccal tubes, thereby to drive the buccal tubes and molars rearwardly. The auxiliary arms comprise means for adjusting the lengths of the auxiliary arms, thereby to adjust the force to be applied against the buccal tubes. The means for adjusting the length desirably comprises hairpin loops in the auxiliary arms.

BRIEF DESCRIPTION OF THE DRAWINGS

Further objects, features and advantages of this invention will become apparent from the following description and drawings, of which

FIG. 2 is an enlarged, partial front perspective view of a portion of the orthodontic arch of FIG. 1;

FIG. 3 is an enlarged, fragmentary perspective view of a portion of FIG. 1, taken generally in the direction indicated by line 3—3 of FIG. 1;

FIG. 4 is an enlarged, fragmentary side elevational view of the face-bow and arch of FIG. 3;

FIG. 4A is an enlarged fragmentary side elevational view essentially the same as FIG. 4, except that the face-bow is shown in the high-pull phantom position of FIG. 1;

DESCRIPTION OF THE PREFERRED EMBODIMENTS

Figure 1:
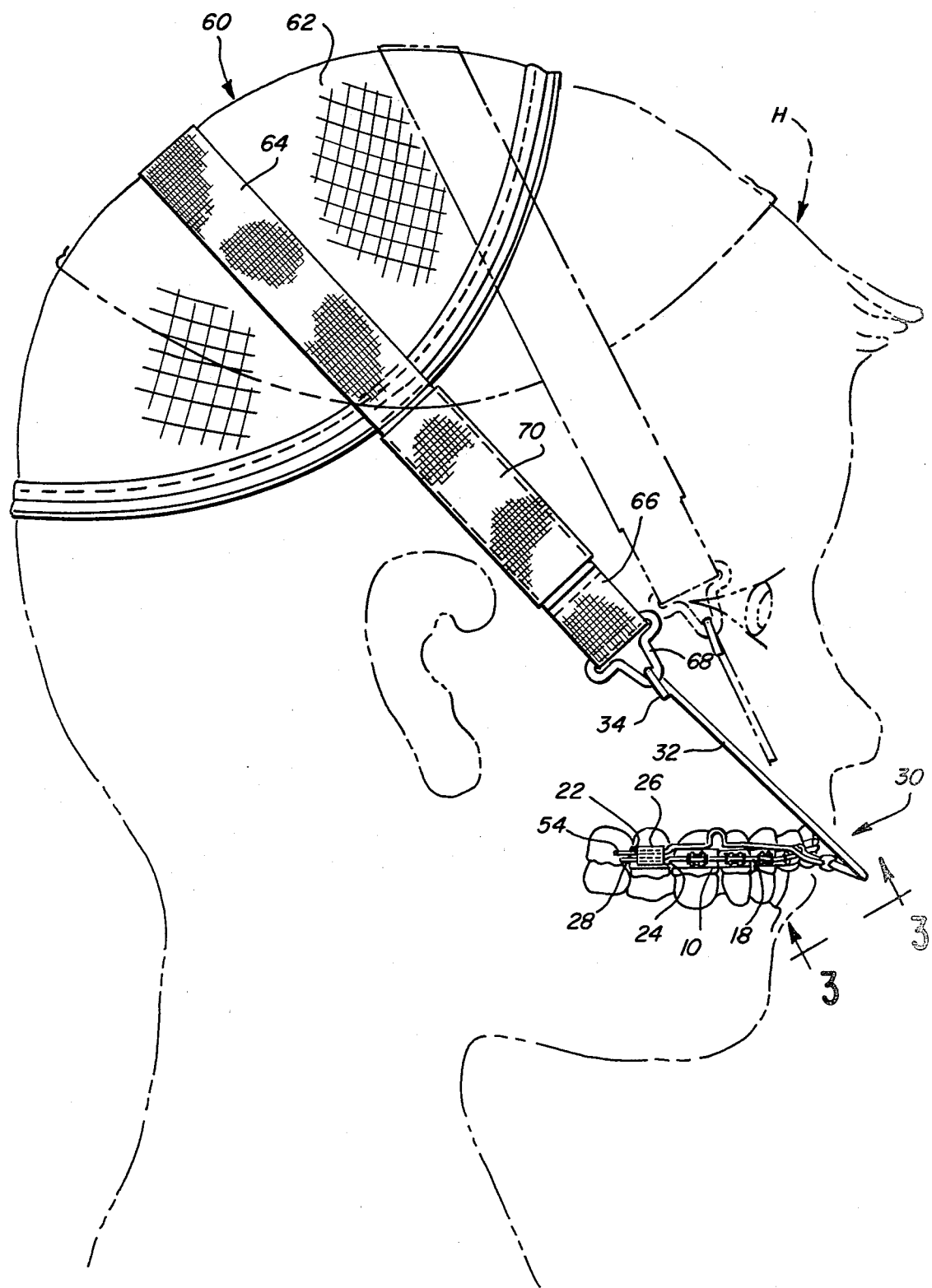
FIG. 1 is a side elevation view of a presently preferred embodiment of the face-bow of this invention showing the face-bow in its operative relationship to an orthodontic arch.

Referring first to FIG. 1, a patient's head H, in phantom, is shown as having a face-bow of this invention fitted therewith. For convenience of illustration and description, the six upper anterior teeth have been designated (in FIG. 2) by the letters CI (central incisors), LI (lateral incisors) and C (canines).

FIG. 1 shows generally an orthodontic arch 10 and a face-bow 12 of this invention. Orthodontic arch 10 includes a plurality of tooth bands 14 (FIG. 2) secured appropriately to the teeth. Each of the bands 14 is provided at its front with a bracket 16. Brackets 16 include upper and lower outwardly extending bracket elements, each of which elements is divided, as seen, into two horizontally spaced segments.

The orthodontic arch wire 18 is disposed between the upper and lower bracket elements of brackets 16. The arch wire illustrated is rectangular in cross-section and is proportioned with respect to the brackets 16 so that it fits snugly between the upper and lower bracket elements. The facing surfaces of the forwardly extending bracket elements, that is the opposed surfaces against which arch wire 18, is disposed are generally flat and parallel to each other to assist in maintaining a snug fit between the bracket elements and the arch wire.

Round arch wires may be used instead for certain techniques and particularly at the beginning of treatment. In fact with many techniques it is desirable to initiate treatment with round arch wires. After an initial leveling off of the teeth, and after the brackets of the teeth are generally coplanar so that bracket engagement is easily made with rectangular arch wires, a rectangular arch wire may be substituted where techniques such as reshaping of the maxilla are employed. In some cases, a round wire may be used throughout treatment, such as where just distal driving or leveling of the teeth is desired. As will be apparent, when light round wires are employed, lighter forces are used. With rectangular wires and with heavy round wires, heavier forces may be employed.

To retain arch wire 18 between the bracket elements, arch wire 18 is secured to each bracket 16, as by a tie wire 20. Tie wires 20 are looped around the arch wire 18 and tied to brackets 16 in a conventional manner readily discernible from FIGS. 2 and 3.

At molar tooth bands 22 on two of the molar teeth (one on each side), the arch wire is provided with stops such as bent wire portions 24 which prevent rearward movement of the arch wire 18 with respect to the molar or buccal tubes 26. Buccal tubes 26 are connected to molar bands 22 in any suitable conventional manner thereby to secure the buccal tubes to a patient's molars. The ends 28 of the arch wire, the portions disposed rearwardly of the stops, are slidably disposed within the buccal tubes. The passages are shown in dotted line.

Figure 5:
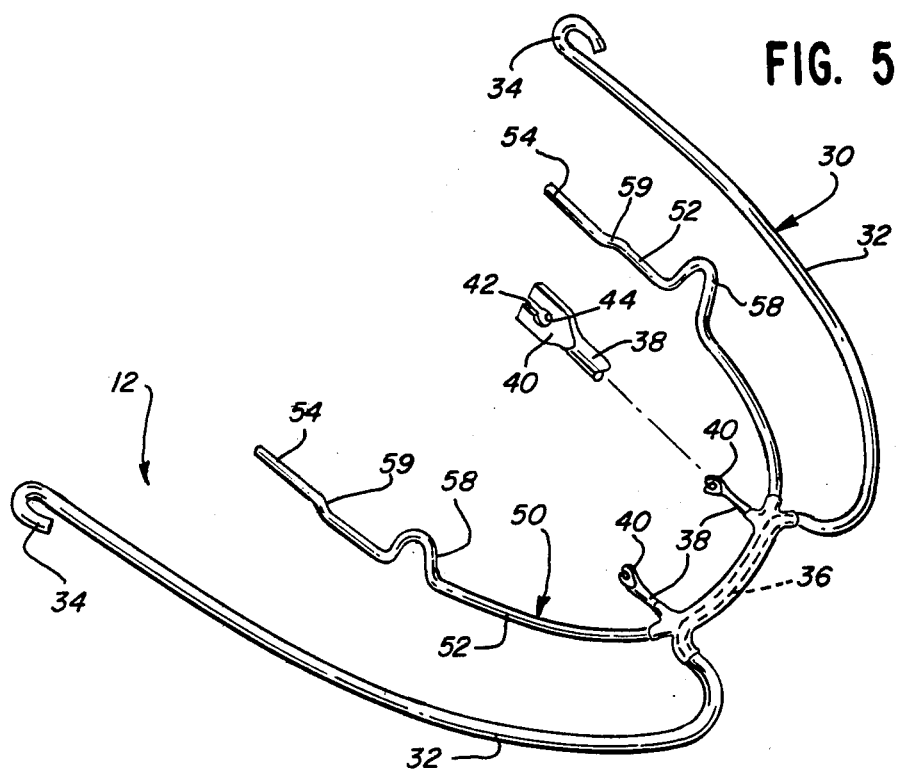
FIG. 5 is a perspective view of a face-bow of this invention.

Face-bow 12 of this invention, as best seen in FIGS. 1–5, comprises a continuous frame portion 30. The face-bow 12 is shown in its generally operative shape and use in FIGS. 1–4A. In FIG. 5 it is shown before being bent to the configurations assumed in FIGS. 1–4A, i.e., for application of forces both horizontal and vertical, and principally vertical, directions, as respectively shown by FIGS. 4 and 4A.

Face-bow frame portion 30 includes a pair of rearwardly and upwardly extending arms 32 terminating in hook means such as hooks 34 at their rear ends. Frame portions 30 also includes a central segment 36 connecting the forward ends of the arms 32 to the frame portion 30 adjacent the central frame portion or segment 36. Face-bow levers 38 are connected to the frame adjacent the central segment 36. Levers 38 may be bent from the FIG. 5 position to angular positions typically shown by FIGS. 3–4A consistent with the treatment desired. Levers 38 may be integral with a central connecting segment or may be separately brazed to the frame portion 30 in a known manner. In any event, the levers and frame portion are integrated with a smooth layer of silver solder. The free end of each of the levers 38 is flattened and reduced in cross-section. The free ends of the levers comprise forks 40. Each fork 40 has a generally rectangular opening or lumen 42. The lumen terminates in a keyhole portion 44 which is large enough to permit free oscillation of the fork relative to the arch wire 18 so that the wire and associated teeth will not be torqued due to testing of the wire.

In addition to the frame portion 30 and levers 38, the face-bow 12 includes an auxiliary arch wire 50. Auxiliary wire 50 comprises a pair of rearwardly extending auxiliary arms 52 which are suitably secured, as with silver solder, adjacent the central frame portion or segment 36. Arms 52 may be integrated through a central member (not shown) or may be separately secured to frame portion 30.

Figure 6:
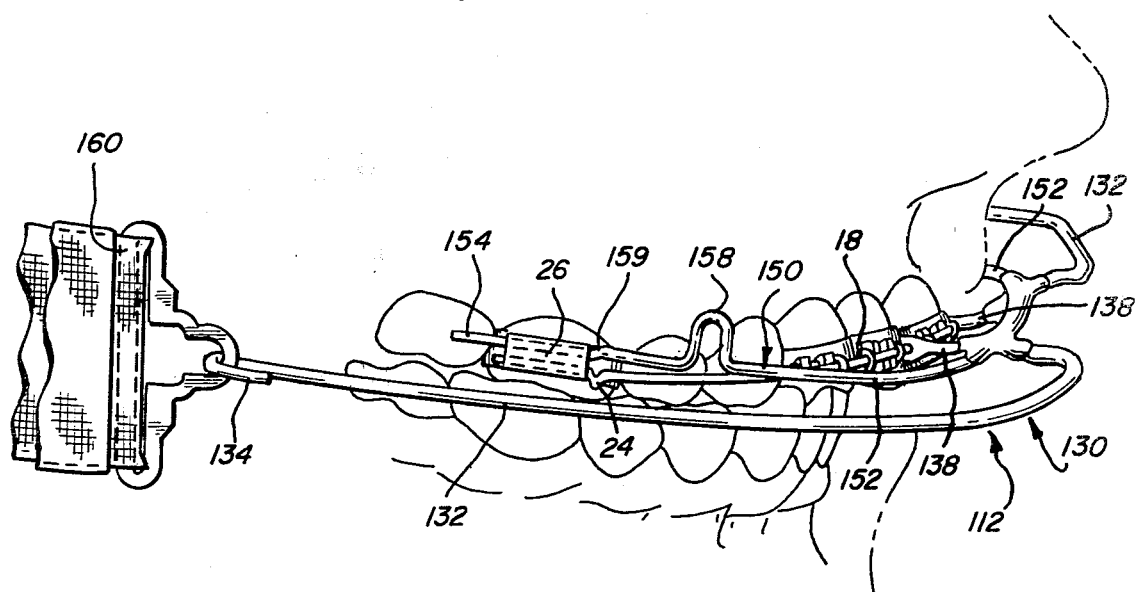
FIG. 6 is a perspective view of a further face-bow of this invention showing it in its operative relationship to an orthodontic arch, and positioned primarily for distal driving.

Auxiliary arms 52 are suitable shaped to lie closely parallel to the arch wire 18 and to extend rearwardly and into engagement with the buccal tubes 26. Tubes 26 define integral openings, generally parallel to the openings receiving ends 28 of the arch wire 18. The ends 54 of arms 52 extend through the openings and beyond, generally as shown in FIGS. 1 and 6, and are therefore removably positioned in association with the respective buccal tubes. The ends 54 are of a length proportioned such that when the levers 38 and forks 40 are moved forwardly from their portions of engagement with the arch wire 18, the ends will remain in engagement with the buccal tubes, for a reason to be explained later. Auxiliary arms 52 also define adjustment means or hairpin loops 58 which adjust the lengths of the arms 52 and the force applied against the buccal tubes and stops comprising bent sections 59. The former are to adjust the forces to be applied to the buccal tubes. The stops 59 act against the buccal tubes to transmit the desired forces against the molars.

To support and hold a face-bow 12 in its desired, predetermined operative relationship with respect to an arch wire 18, and to activate the face-bow, a head harness 60 may be provided. Head harness 60 may include a cap 62 fabricated of a loose mesh or netting such as a nylon netting. Adjacent the center of the cap, and extending laterally and across the cap and connected thereto, is a narrow strip 64 of stout, non-stretchable material, such as a one inch strip of grosgrain. Strip 64 terminates at each side adjacent the perimeter of the cap and provides the main force bearing portion of the head harness 60. The cap portion serves to assist in maintaining predetermined positioning of the strip 64.

Strip 64 also provides the means for connecting elastic, tension-exerting straps 66 to the head harness. Each strap 66 is sewn to the strip 64 and extends downwardly as is seen in FIG. 1. The lower ends of tension exerting straps are connected to strap hooks 68. The length of the straps 66 may be varied as desired to give the indicated degree of tension or pull. When the proper length has been determined, portions of the elastic straps 66 will overlie other portions and may then be connected to each other, as by stitching. Satin sleeves 70 are disposed to surround straps 66 and are slidably mounted on those straps. Sleeves 70 are utilized as those portions of the head harness 60 which bear against the sides of the face to prevent abrasion of the face by the straps 66. A head harness of this type is described in U.S. Pat. No. 3,186,089.

Strap hooks 68 provide the medium for connecting the hooks 34 of a face-bow 12 to the head harness for applying forces against the arch wire 18 via the levers 38 which are removably connected to the arch wire. The degree of tension desired may be varied by increasing or decreasing the lengths of straps 66 in the manner described. Substantial strong, vigorous forces may be used when modification of and change in the configuration of the maxilla itself is desired, while lesser forces may be used to obtain other types of correction, some of which are referred to herein. However, the threshold of pain limits the amount of force which may be used. At no time should there be any pain with the use of the face-bow of this invention.

Although an orthodontic arch 10 has been described in some detail, the arch used in the practice of this invention need not be identical to that illustrated in FIGS. 1–4A. A variety of arches may be used and may be fitted in any manner familiar to those of ordinary skill in the art. While the embodiment illustrated includes an arch wire which is rectangular in cross-section, round arch wires may also be used at various stages of treatment or with other techniques.

As stated, the forces necessary to carry out the corrective techniques described herein are imparted to the teeth through the suitably adjusted face-bow 12. A face-bow 12 embodying the principles of this invention may be fabricated from 304 stainless steel wire and silver solder to assist in connecting the elements and to aid in reinforcing the central segment 36.

A dentist or orthodontist desiring to correct a case of deep overbite, wishing to flatten a steeply pitched occlusal plane, desiring to modify the maxillary bone structure or otherwise wishing to correct a condition requiring treatment will first apply an appropriate orthodontic arch.

The orthodontist should then obtain a suitably sized and proportioned face-bow 12 and should make the necessary final adjustments for the individual patient. The orthodontist should take into consideration, among other things, the shape of the patient's mouth, the size of his head, the shape and dimensions of the patient's lips, the size and spacing of his teeth, and, of course, the type of condition to be treated. The nature of the changes in the face-bow 12 to be made will be apparent from the description herein, and will depend in part upon the techniques practiced and the results desired.

The high-pull corrective technique, that of correcting deep overbites and flattening steeply pitched occlusal planes, for which the face-bow of FIGS. 1–5 is particularly adapted, requires a substantial vertical component of force to be applied to the arch wire 18. As seen in FIG. 4, the angle of the force applied to the arch wire 18 is about 45°. Thus the vertical and horizontal components of force will be approximately equal. The vertical component tends to drive the upper teeth, particularly the anterior teeth, upwardly.

As will be apparent, whether the face-bow is in a full high-pull orientation as shown in FIG. 4A or in a position in which there is a more moderate vertical component of force (as in FIG. 4), some torquing of the upper anterior teeth occurs. That is because the force is applied to the brackets which are spaced from the axes of the teeth. The greater the upward component of force, the greater the torquing effect. Of course, additional torquing will occur if the wire itself is torqued by the lever forks. The extent to which the torquing effect is to be made use of will depend upon the treatment chosen by the orthodontist.

As will be appreciated from the foregoing description, a horizontal component of force be exerted against the teeth by the face-bow 12. The horizontal component drives the anterior teeth distally, i.e., rearwardly, and with the auxiliary arch wire 50, will also act simultaneously to drive the molars rearwardly as well.

With early "high-pull" techniques, it was not possible to exert effective pressures in excess of a few ounces. With the face-bow shown in U.S. Pat. No. 3,186,089, it became possible to apply strong, vigorous forces, i.e., forces of as much as four to eight ounces. By using the teeth and their roots as levers, the orthodontist was enabled to exert pressures sufficient to alter and to physically modify the maxillary bone structure so that the shape of the maxilla was gradually and permanently changed.

Because such face-bows embodied a rigid reinforced central portion, and incorporated stout rearwardly extending levers which were relatively immobile with respect to the central portion, the orthodontist was enabled to treat the entire maxilla as a unit, thereby to facilitate its permanent reshaping and modification whereby a more permanent correction of malocclusion and a more aesthetic appearance was obtained.

By permanently altering the maxilla, it was frequently possible to bring about permanent and complete correction in very deep overbite cases, something very difficult or almost impossible with earlier corrective appliances and techniques. Of course, the younger the patient involved, the greater the degree to which, and the speed with which, structural changes in the maxilla were made.

The face-bow of this invention continues to to facilitate rapid treatment and correction of such conditions. Indeed by combining maxillary modification in the anterior region with simultaneous distal driving of the molars (without requiring extraction of bicuspids in some cases or preliminary opening of space before relocation of the anterior segment), the face-bow 12 produces enhanced corrective capabilities. Additionally, the face-bow very importantly provides increased assurance against physical damage to a patient's face and eyes. In this regard, in the very recent past several instances of eye and face injury have occured as a result of misusing or improperly using prior art face-bows. It appears that with some types of face-bows, levers were disengaged from the arch wire without first disengaging the elastic strap. When this occured, particularly in high-pull applications, and the levers were moved outwardly of the mouth by the patient and inadvertently released, the bow and levers contacted the face and in several cases contacted eyes, causing grievous injury. Whether such occured at night accidentally while a patient was sleeping or deliberately during the day, the result was disastrous when the slingshot effect of the elastic caused the face-bow and levers to contact the patient's face and eyes.

The addition of the auxiliary wire 50 connected to the buccal tube makes it virtually impossible to remove the face-bow with the elastic or strap connected to the bow. The substantial length of the safety wire arm ends, as much as $\frac{1}{8}$" or more combined with the buccal tube length of at least $\frac{1}{8}$" to $\frac{1}{4}$", means that the face-bow must be drawn forwardly at least $\frac{1}{4}$" or more before it is free of the buccal tubes. Beyond that, because the auxiliary wire will remain in the mouth, it is impossible for the bow to "shoot" upwardly. The bow must be withdrawn forwardly at least about 3 to 4 inches before it can be removed from the mouth. The elastic of a strap 66 cannot be stretched that far. As such, the types of face and eye injuries discussed which have occured in the past cannot be replicated.

In the embodiment illustrated and described in FIGS. 1-5, techniques utilizing both vertical and horizontal components of force have been discussed. Indeed the angle at which the levers engage the wire may be changed to substantially vertical, at which the strap should be moved forwardly as is illustrated in phantom in FIG. 1 and by FIG. 4A. The levers may be moved to engage the wire 18 at other angles between vertical and horizontal.

In accordance with the present invention, where indicated, distal driving via the application of substantially only a horizontal component of force against a wire 18 may be accomplished. That may be done, as shown in FIG. 6, by substituting a neck strap 160 for head harness 50, i.e., a strap which passes around a patient's neck rather than his head. In such a case levers 138 will be angled so that substantially all of the force transmitted by them to an arch wire 18 is exerted in a plane generally normal to the axes of the teeth.

As shown in FIG. 6, an orthodontic arch 10 is adapted to be acted on by a face-bow 112. Bands 14 having brackets 16 are provided. Bands 14 mount a suitable arch wire 18 which is secured to brackets 16 as by suitable tie wires. Molar tooth bands mounting buccal tubes 26 are provided. The arch wire 18 may be secured with the buccal tubes with a bent arch wire position 24.

Face bow 112 may comprises a frame portion 130 having arms 132 and hooks 134. A central frame portion segment is integrated with the arms 132 and a pair of face-bow levers 138 are secured thereto and extend rearwardly therefrom. Each lever 138 mounts a fork 140 which defines a rectangular lumen and keyhole configuration portion like those of the face-bow 12, and for the same purposes.

Face bow 112 also incorporates a safety or auxiliary wire 150. Like wire 50, wire 150 includes arms 152, arm ends 154, hairpin bends 158 and stop segments 159. Stop segments 159 bear against the buccal tubes 26, to limit rearward movement, therefore to act against the tube itself to drive buccal tubes 26, hence the associated molars, rearwardly to open space in the arch segment, as necessary. The force applied by the stop segment 159 may be adjusted via the hairpin bend 158, as described above. Thus, although in the first instance the forks 140 limit the depth of penetration of the arm ends 154, supplemental and simultaneous distal driving of the molars may be accomplished via bend 158 and stop segment 159. Yet, the safety features of the present invention are present in substantially the same manner as in the embodiment of FIG. 1, i.e., the face-bow 112 of FIG. 6 may not be removed from the mouth and lifted upwardly and then released to contact the eyes without first disengaging the strap 160.

The foregoing description of presently preferred embodiments of my invention will make obvious to those skilled in the orthodontic art the fact that various changes may be made in the embodiments illustrated and described without departing from the spirit and scope of the invention. Therefore I do not intend to be limited to the embodiments illustrated. Rather I intend that the scope of the invention shall be construed as broadly as may be permitted by the appended claims.

What Is claimed is:

1. An orthodontic face-bow for preventing facial and eye injury and adapted to apply force to a patient's teeth through an orthodontic arch fixed to the patient's teeth and adapted to be removably connected to said arch, said face-bow comprising a frame having a pair of rearwardly extending arms each terminating in hook means at the rear end and in a central frame portion at their forward ends, spaced levers secured to said frame adjacent said central frame portion, each of said levers extending upwardly and being removably connectable to said arch by a fork portion having a generally rectangular lumen which terminates in a keyhole portion, and an auxiliary arch wire secured to said frame adjacent said central frame portion, said auxiliary arch wire comprising auxiliary arms extending rearwardly from said central frame portion, each auxiliary arm having an end portion adapted to be removably positioned in association with a buccal tube fixed to a molar for securing said face-bow against removal from a patient's mouth.

2. An orthodontic face-bow in accordance with claim 1 wherein said spaced levers extend upwardly from where they are secured to said frame.

3. An orthodontic face-bow in accordance with claim 1 wherein said orthodontic arch includes brackets secured to a patient's teeth, buccal tubes secured to a patients's molars and an arch wire secured to said bracket and buccal tubes, and wherein said end portions of said auxiliary arms are removably disposed in passages in said buccal tubes.

4. An orthodontic face-bow in accordance with claim 3 wherein said auxiliary arms comprise means adjacent said auxiliary arm end portions for bearing against and applying force against said buccal tubes to drive said buccal tubes rearwardly.

5. An orthodontic face-bow in accordance with claim 4 wherein said auxiliary arms comprise means for adjusting the lengths of said auxiliary arms to adjust the force to be applied against said buccal tubes.

6. An orthodontic face-bow in accordance with claim 5 wherein said means for adjusting the length comprises hairpin loops in said auxiliary arms.

7. A face-bow positioned for preventing facial and eye injury and to apply force to a patient's teeth through an orthodontic arch fixed to the patient's teeth and removably connected to said arch, said orthodontic arch comprising brackets secured to anterior teeth and buccal tubes secured to molars, and an arch wire connected to said brackets and buccal tubes, said face-bow comprising a frame having a pair of rearwardly extending arms each terminating in hook means at the rear end and in a central frame portion at the forward ends, rearwardly and upwardly extending spaced levers secured to said frame adjacent said central frame portion and each lever terminating with a fork portion having a generally rectangular lumen which terminates in a keyhole portion, each of said levers being removably connected to said arch wire, and elastic means secured to said hook means and about said patient's head to cause said levers to forceably bear against said arch wire, and an auxiliary arch wire secured with said frame adjacent said central frame portion, said auxiliary arch wire comprising auxiliary arms extending rearwardly from said central frame portion, each auxiliary arm having an end portion removably positioned in association with a buccal tube, whereby said face-bow is secured against removal from a patient's mouth without first removing said elastic means.

8. The combination of claim 7, and wherein said auxiliary arms comprise means adjacent said auxiliary arm end portions bearing against and applying force against said buccal tubes for driving said buccal tubes rearwardly.

9. The combination of claim 8, and wherein said auxiliary arms comprise means for adjusting the lengths of said auxiliary arms to adjust the force to be applied against said buccal tubes.

10. The combination of claim 9, and wherein said means for adjusting the lengths of said auxiliary means comprises hairpin loops in said auxiliary means.

11. A method of preventing eye and facial injuries while altering the alignment and positioning of teeth with a face-bow comprising the steps of positioning a removably connectable face-bow to apply force to a patient's teeth through an orthodontic arch fixed to the patient's teeth, said orthodontic arch comprising brackets secured to anterior teeth and buccal tubes secured to molars and an arch wire connected to said brackets and buccal tubes, said face-bow comprising a frame having rearwardly extending arms each terminating in hook means at the rear end and in a central frame portion at the forward end, spaced levers secured to said frame adjacent said central frame portion, each of said levers being removably connected to said arch wire, said face-bow further including an auxiliary safety arch wire secured with said frame adjacent to said central frame portion, said auxiliary arch wire comprising auxiliary arms extending rearwardly from said central frame portion, each auxiliary arm having an end portion removably positioning each said end portion in association with a buccal tube, and connecting elastic means secured to said hook means and positioned about said patient's head to cause said levers to forceably bear against said arch wire, whereby said face-bow is safely secured against removal from a patient's mouth without first removing said elastic means.

12. The method of claim 11 wherein said buccal tubes define passages, and wherein said step of positioning said end portions in association with said buccal tubes comprises inserting the end portions in said buccal tubes.

13. The method of claim 12 wherein said face-bow comprises fork means at the ends of said levers, and said step of positioning said face-bow comprises securing said forks to said arch wire.

14. The method of claim 12, and wherein said auxiliary arms comprise means adjacent said auxiliary arm end portions for bearing against and applying force against said buccal tubes, and the further step of thereafter driving said buccal tubes and associated molars rearwardly.

* * * * *